United States Patent [19]
Lund

[11] Patent Number: 5,402,585
[45] Date of Patent: Apr. 4, 1995

[54] STADIOMETER

[76] Inventor: Marvin S. Lund, 5322 Frost Point Cir., Prior Lake, Minn. 55372

[21] Appl. No.: 142,230

[22] Filed: Oct. 25, 1993

[51] Int. Cl.[6] .............................................. G01B 5/00
[52] U.S. Cl. .................................... 33/832; 33/434; 33/512
[58] Field of Search ................. 33/832, 406, 407, 427, 33/464, 484, 512

[56] References Cited

U.S. PATENT DOCUMENTS

| | | | |
|---|---|---|---|
| 442,192 | 12/1890 | Lewis | 33/512 |
| 1,860,184 | 5/1932 | Jacobs | 33/512 |
| 2,028,052 | 1/1936 | Easterly | 33/427 |
| 2,215,884 | 9/1940 | Runge | 33/512 |
| 3,313,030 | 4/1967 | Heys | 33/512 |
| 3,522,655 | 8/1970 | Kilpatrick et al. | 33/464 |
| 4,121,344 | 10/1978 | Goussios | 33/427 |
| 4,134,213 | 1/1979 | Kushmuk | 33/512 |
| 4,155,168 | 5/1979 | DuBois | 33/760 |

FOREIGN PATENT DOCUMENTS 2244143 11/1991 United Kingdom ................. 33/427

*Primary Examiner*—William A. Cuchlinski, Jr.
*Assistant Examiner*—G. Bradley Bennett
*Attorney, Agent, or Firm*—Burd, Bartz & Gutenkauf

[57] ABSTRACT

A stadiometer for measuring height of a person to the nearest millimeter and sixteenth-of-an-inch has an upright rail movably supporting a slide carrying a height measuring arm. A scale on the rail is covered with a transparent shield connected to the slide. A line on the shield aligned with the arm is used to read the scale to provide height data of a person.

27 Claims, 4 Drawing Sheets

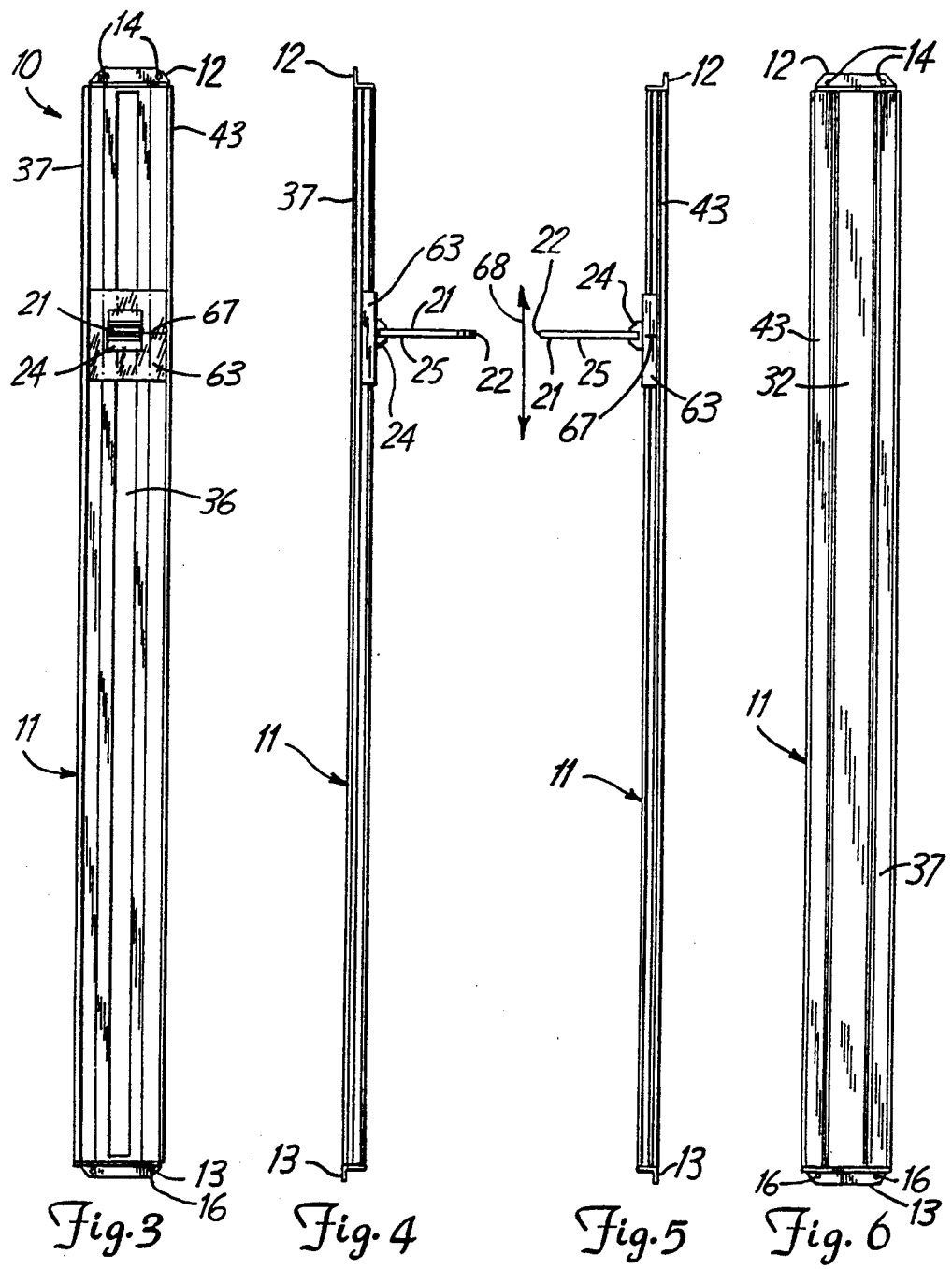

STADIOMETER

FIELD OF INVENTION

The invention is related to the art of measuring the height of an object. This art includes a stadiometer for measuring the height of a primate including humans in English and metric graduations.

BACKGROUND OF INVENTION

Physicians and health care providers routinely measure and record a person's height and weight during physical examination and health check-ups. Records as to the height of a person are monitored according to the English scale in the United States of America and the metric scale in the remaining areas of the world. This dual scale system of the height of the population makes data comparisons time consuming and costly. Vertical scales called stadiometers are used to measure a person's standing and sitting height. The scale graduations are located on upright supports attached to vertical walls. Arms movably mounted on the support are adapted to engage the top of the heads of persons located adjacent the scales to provide information data concerning the height of the persons. This data is incorporated in the persons medical records for use by the medical personnel.

SUMMARY OF THE INVENTION

The invention relates to an apparatus for measuring the height or vertical length of objects, plants, animals and primates, including humans. The apparatus has an upright rail having at least one side section. A scale having vertically-spaced graduations, used to provide information as to the height of the object, is on the side section of the rail. A slide supporting a generally horizontal arm is movably mounted on the rail. A shield mounted on the slide has a transparent portion located over the scale to protect the scale and allow visual reading of the scale. A line on the shield aligned with the arm and extended horizontally over the scale, is used to provide visual information of the location of the arm relative to the scale thereby providing data as to the height of the object when the arm engages the top of the object.

A preferred embodiment of the invention is a stadiometer for measuring the height of a human to the nearest millimeter and sixteenth-of-an-inch. The stadiometer has an upright rail with central upwardly extended side walls that converge outwardly forming a vertical dove tail-shaped groove or track. The rail has side sections that project laterally, outwardly and rearwardly from the side walls. An upright scale is attached to one of the side sections. The scale has English and metric graduations located in vertical side-by-side relation with equivalent graduations laterally aligned with each other. A slide having inwardly diverging walls located adjacent the side walls of the rail, is located within the vertical dove tail-shaped groove. A spring located in the groove behind the slide biases the slide walls into sliding surface engagement with the side walls of the rail. Low friction material associated with the slide walls facilitate sliding movement of the slide along the rail under all environmental conditions. An outwardly projected horizontal arm is secured with a holder to the slide. The arm has a length and size adapted to contact the crown of a person's head during height measurement. A shield, mounted on the slide between the holder and slide, has a transparent portion located over the scale to protect the scale and allow visual reading of the scale. A horizontal line on the shield aligned with the bottom surface of the arm, is used to provide visual information or data concerning the location of the arm relative to the scale thereby providing data of the height of the person when the arm contacts the crown of the head of the person.

The stadiometer is a durable height measuring apparatus that has a height measuring arm that moves smoothly, without binding, on the rail under all environmental conditions. The scale is easy to read in both English and metric graduations from 21 inches to 84 inches, or 533 mm to 2134 mm. Other features and advantages of the stadiometer are embodied in the following detailed description thereof.

DESCRIPTION OF DRAWINGS

FIG. 3 is a front elevational view thereof;

FIG. 4 is a left side elevational view thereof;

FIG. 5 is a right side elevational view thereof;

FIG. 6 is a rear elevational view thereof;

DESCRIPTION OF PREFERRED EMBODIMENT

Referring to FIGS. 1-6, there is shown an apparatus for measuring the height of an object, shown as a stadiometer for measuring standing or sitting height of a primate including humans, to the nearest millimeter and sixteenth-of-an-inch. Animals and plants can also be measured with the apparatus. Stadiometer 10 is mounted on an upright support, such as a wall, above a flat floor commonly found in medical and health care facilities and health care fitness centers.

Figure 8:
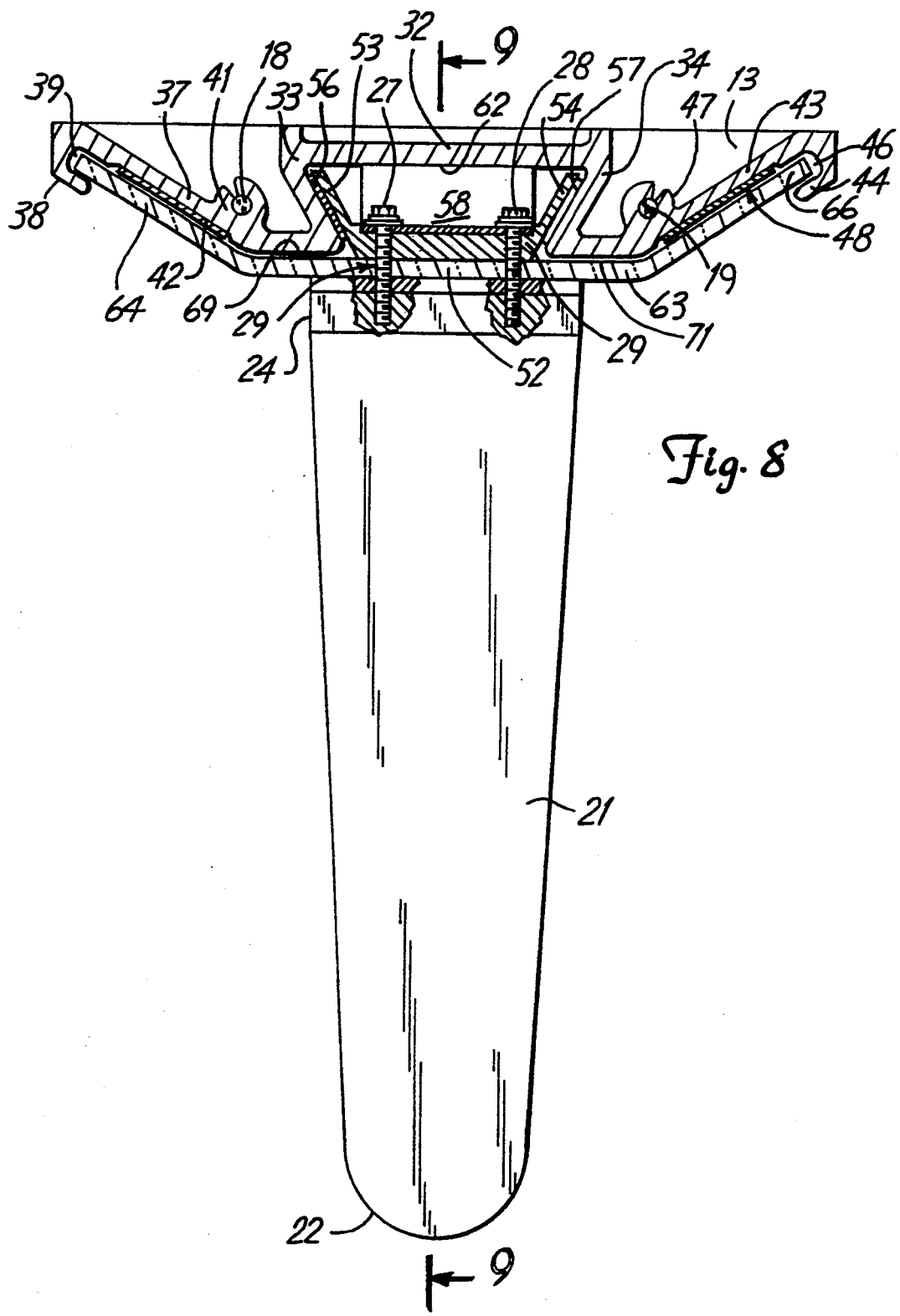
FIG. 8 is an enlarged sectional view taken along the line 8—8 of FIG. 1.

Stadiometer 10 has an upright rigid rail, indicated generally at 11, connected at its opposite ends to an upper mounting bracket 12 and a lower mounting bracket 13. Brackets 12 and 13 have pairs of holes 14 and 16, respectively, to accommodate fasteners, such as screws and bolts used to attach stadiometer 10 to a support. A plurality of bolts 17 secure mounting brackets 12 and 13 to opposite ends of rail 11. As seen in FIG. 8, rail 11 has projections 42 and 47 containing upright holes 18 and 19 for accommodating bolts 17. Other fastening structures can be used to mount brackets 12 and 13 on opposite ends of rail 11.

Figure 9:
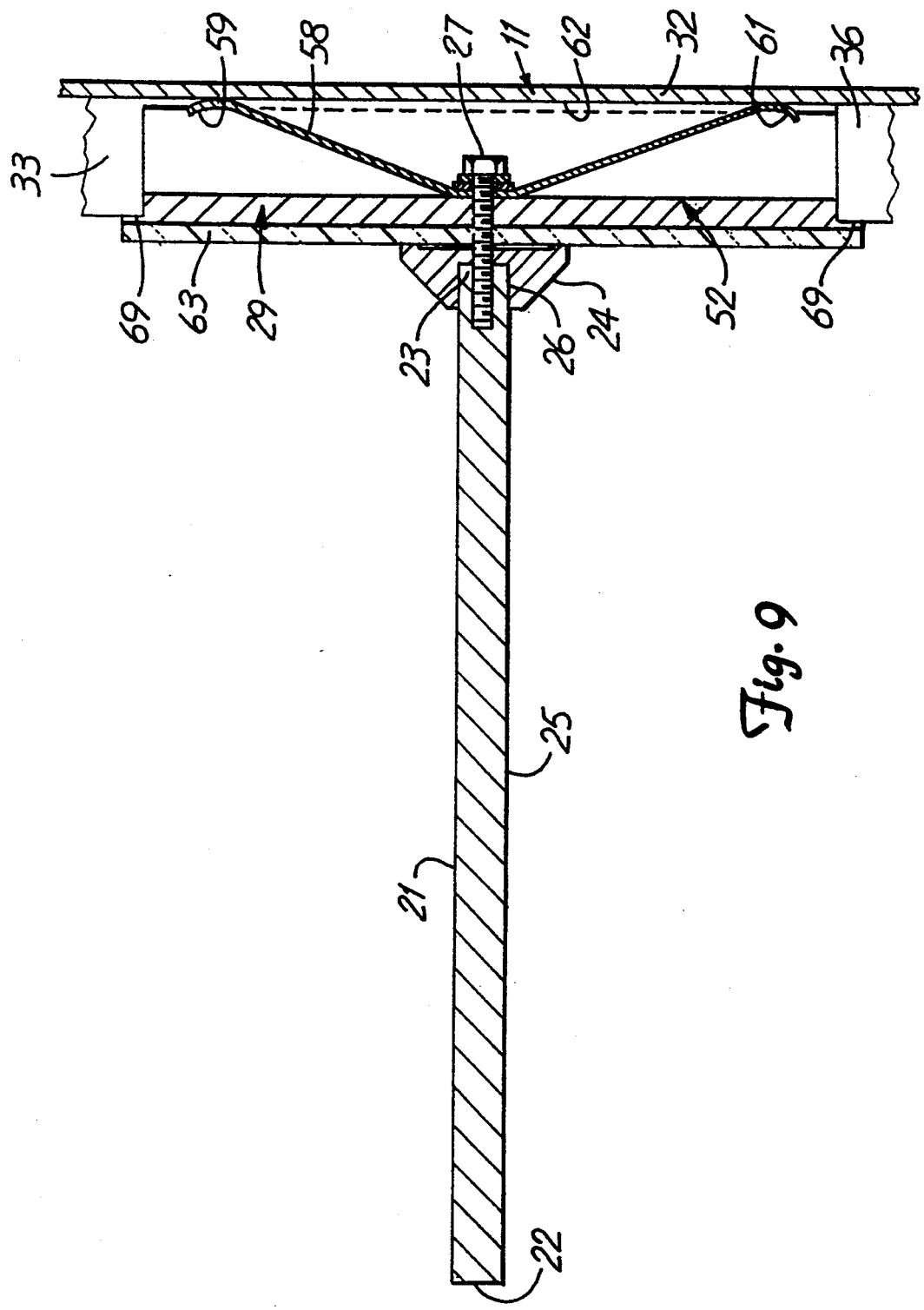
FIG. 9 is a sectional view taken along the line 9—9 of FIG. 8.

Rail 11 movably supports a generally horizontal arm 21 having an outer rounded end 22, an inner end 23 and a flat bottom surface 25. As seen in FIG. 9, inner end 23 is connected to a holder 24 having a transverse slot 26 to provide arm 21 with vertical and lateral stability. Holder 24 maintains the horizontal orientation of arm 21 in its adjusted positions along the length of rail 11. Arm 21 is moved along rail 11 until it contacts the crown of a person's head to measure the height of the person. End 23 telescopes into slot 26 and is retained therein by bolts 27 and 28. Bolts 27 and 28 are also connected to a slide, indicated generally at 29, movably mounted on rail 11.

Referring to FIGS. 8 and 9, rail 11 has a flat upright central section 32 joined to outwardly projected and inwardly inclined side walls 33 and 34 providing linear tracks and forming an upright dove tail-shaped groove or channel 36. A first side section 37 extends laterally and inwardly from side wall 33 at an angle of about 30° from the front surface and terminates in a reverse turned ear 38 providing an upright groove 39 along one side of rail 11. A projection 41 is secured to the back side of side section 37. An upright decorative tape 42 is attached to the outside surface of side section 37. A second side section 43 extends laterally and rearwardly from the outer portion of side wall 34 and terminates in an outer end having a reverse turned flange 44 forming an upright groove 46. Slide section 43 projects rearwardly at an angle of 30° so that scale 48 is easy to read. Projection 47 is attached to the inside of side section 43. An upright scale, indicated generally at 48, is attached to the outside surface of side section 43.

Figure 7:
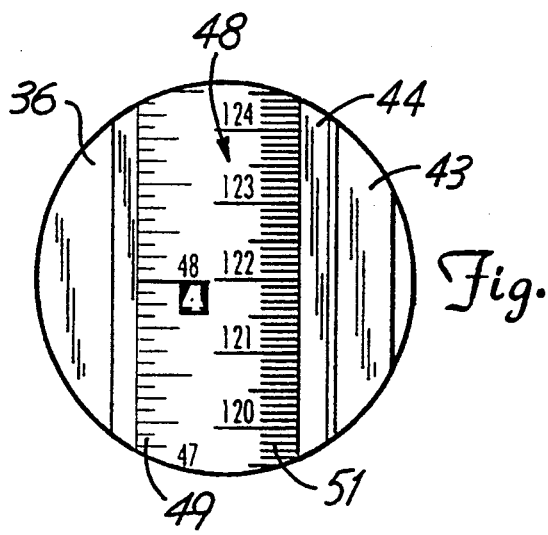
FIG. 7 is an enlarged portion of the English-metric scale, as indicated at 7 in FIG. 1.
Figure 2:
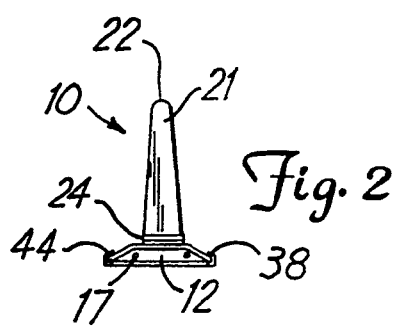
FIG. 2 is a top plan view of thereof.

As shown in FIG. 7, scale 48 has English calibrations 49 and corresponding metric calibrations 51. The English calibrations are in one-sixteenth-of-an-inch increments or graduations. The metric graduations or calibrations are in millimeters. The calibrations are represented with horizontal lines. The English calibration lines extend horizontally from the left side of scale 48. The metric calibration lines extend horizontally from the right side of scale 48. The English calibration lines that correspond to the metric calibrations lines are horizontally aligned. Scale 48 measures heights from 21 inches to 84 inches or 533 millimeters to 2,134 millimeters. The English and metric scales are of different colors to provide for visual distinction and ease of reading the scales. For example, the English scale has red calibration lines while the metric scale has blue calibration lines.

As shown in FIGS. 8 and 9, slide 29 has a generally flat upright base 52 joined to rearwardly and outwardly diverging side walls 53 and 54 that have angles that are complimentary to the converging angles of side walls 33 and 34 of rail 11. Strips of low-friction tapes 56 and 57, secured to the outside surfaces of side walls 53 and 54, are located in sliding surface engagement with the inside flat surfaces of tapered side walls 33 and 34. Tapes 56 and 57 are located in shallow recesses in side walls 53 and 54 and extend the full length of side walls 56 and 57. The tapes 56 and 57 can be Teflon tapes having adhesive surfaces that secure the tapes to slide side walls 53 and 54. Other types of low-friction materials including low-friction coatings can be used on the outside surfaces on side walls 53 and 54 to ensure the smooth movement of slide 29 and arm 21 along side walls 33 and 34.

As shown in FIG. 9, a biasing device, shown as bowed leaf spring 58, is secured with bolts 27 and 28 to base 52 of slide 29. Spring 58 has reverse turned or arcuate-shaped ends 59 and 61 located in sliding friction engagement with vertically spaced portions of inside surface 62 of back wall 32 of rail 11. Spring 58 biases slide 29 in an outward direction holding the low-friction tapes 56 and 57 in firm sliding surface engagement with the inside surface of side walls 33 and 34 of rail 11. Tapes 56 and 57 have elongated rectangular flat outer faces located in surface engagement with side walls 33 and 34, which prohibits angular movement of arm 21, so that arm 21 remains horizontal during movement of slide 29 along rail 11. The converging side walls 33 and 34 prevent slide 29 from separating from rail 11.

Figure 1:
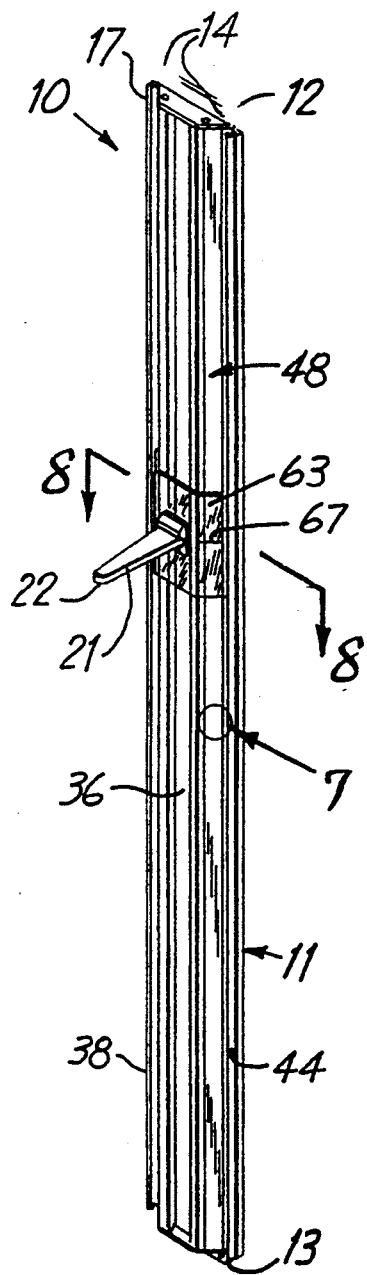
FIG. 1 is a front perspective view of the stadiometer of the invention.

A shield, indicated generally at 63, of rigid and transparent plastic material, such as transparent polycarbonate, is interposed between support 24 and slide 29. As seen in FIG. 8, base 52 of slide 29 projects a short distance out of groove 36 to space the inner surface of shield 63 from rail surfaces 69 and 71, tape 42 and scale 48. Shield 63 does not rub on rail 11, tape 42 or scale 48. Shield 63, being spaced from scale 42, does not move nor scratch the outer surface of scale 42. Bolts 27 and 28 extend through aligned holes in shield 63 and support 24 and into threaded holes in the inner end of arm 21 so that shield 63 is clamped between support 24 and slide 29 thereby fixing the position of shield 63 in spaced relation relative to rail surfaces 69 and 71, tape 42 and scale 48. Shield 63 moves with slide 29 and arm 21, along rail 11. As shown in FIGS. 1, 3 and 5, shield 63 has a horizontal site line 67 horizontally aligned with the bottom surface 25 of arm 12 and extends to the right edge of shield 63 over scale 48 whereby bottom surface 25 of arm 21 when in engagement with the crown of a person's head, provides the height measurement of a person on scale 48 in English and metric numbers. Shield 63 has opposite lateral and rearwardly directed sections having ends 64 and 66 that extend into grooves 39 and 46, respectively, thereby protecting opposite edges of shield 63 and maintains shield 63 close to decorative tape 42 and scale 48. Lips 38 and 44 also cover the outer edges of shield 63 so that these edges cannot injure a patient or medical persons. Lips 38 and 44 further prevent bending and breakage of shield 63 as the outer edges of shield 63 cannot be pulled away from rail 11. Shield 63, being transparent, provides for protection, as well as visual observation of decorative tape 42 and scale 48. Rail 11 has upright generally flat surfaces 69 and 71 adjacent opposite vertical portions of side walls 33 and 34 that are located adjacent opposite vertical portions of the inside surface of shield 63.

In use, the stadiometer 10 is mounted on a vertical support, such as a wall, above a hard surface floor. Fasteners (not shown) are used to attack brackets 12 and 13 to the support. A carpenter's level is used to ensure that rail 11 is plumb or vertical. A rod having a length of 35 inches, can be used to determine the height of the stadiometer 10 above the floor. The 35 inch mark on scale 48 is aligned with the top of the 35 inch rod to ensure proper location of stadiometer 10 on the wall.

A person's height is measured by locating the person standing with his or her back to stadiometer 10. Arm 21 is moved down until it contacts the crown of the person's head. The health person reads scale 48 in English and metric data, as indicated by the location of line 67 relative to scale 48. This data is incorporated in the person's medical records for use by the medical personnel.

While preferred forms and arrangements of structures have been shown and described, it is intended that various changes in structure, arrangement of structure and materials may be made without departing from the invention as defined in the following claims.

I claim:

1. A stadiometer for measuring the height of a primate comprising: an upright rail having upright side walls that converge relative to each other and a back wall forming an upright groove, and side sections extended laterally from each of said side walls, scale means having English and metric graduations on one of said side sections, slide means engageable with and movable along said side walls, said slide means having walls located in friction sliding engagement with said side walls of the rail whereby the slide means maintains its adjusted position on the rail and is manually movable to a selected position on the rail, biasing means located in said groove and engageable with said rail to bias the walls of the slide means in friction sliding engagement with said side walls of the rail, means securing the biasing means to said slide means, a generally horizontal arm secured to said slide means and extended outwardly from said rail, shield means extended over the scale means, means securing the shield means to the slide means, said shield means being movable with the slide means along said rail and relative to the scale means, said shield means having at least a transparent portion located over the scale means whereby the scale means is visible, and means on said shield means aligned with the arm to provide visual information of the location of the arm relative to the scale means thereby providing measurement data of the height of a primate when the arm engages the top of the head of a primate.

2. The stadiometer of claim 1 wherein: the side sections of the rail project rearwardly and laterally away from the side walls, said shield means having portions extended over said side sections of the rail and the scale means.

3. The stadiometer of claim 1 wherein: the English and metric graduations are located in vertical side-by-side relation with equivalent graduations laterally aligned with each other.

4. The stadiometer of claim 1 including: holder means supporting the arm, and means connecting the slide means to the arm and retaining a portion of the arm on the holder means.

5. The stadiometer of claim 4 wherein: the holder has a transverse groove, said arm having an end located in said transverse groove and retained by said means connecting the slide means to the arm.

6. The stadiometer of claim 4 wherein: the shield means has a portion located between the holder means and slide means, said means connecting the slide means to the arm clamping the shield means between the holder means and slide means.

7. The stadiometer of claim 1 including: low friction means located between said side walls of the rail and the diverging walls of the slide means to facilitate movement of the slide means relative to the rail.

8. The stadiometer of claim 7 wherein: the low friction means is a plastic tape secured to said walls of the slide means and engageable with said side walls of the rail.

9. The stadiometer of claim 1 wherein: the biasing means comprises a leaf spring having opposite ends engageable with the rail.

10. The stadiometer of claim 1 wherein: the side walls of the rail converge outwardly toward each other, said slide means having walls located adjacent said side walls of the rail.

11. The stadiometer of claim 10 wherein: the biasing means comprises a leaf spring connected to the slide means, said leaf spring having ends located in sliding engagement with the back wall of the rail to retain the walls of the slide means in friction sliding engagement with said slide walls of the rail.

12. The stadiometer of claim 10 wherein: the slide means has a base projected outwardly from the rail, said shield means having a portion mounted on the base whereby the shield means is retained in spaced relation relative to the rail and scale means.

13. The stadiometer of claim 10 including: low friction means located between said side walls of the rail and the walls of the slide means to facilitate movement of the slide means relative to the rail.

14. The stadiometer of claim 13 wherein: the low friction means is a plastic tape secured to said diverging walls of the slide means and engageable with said side walls of the rail.

15. The stadiometer of claim 10 wherein: the rail has opposite upright edge means having upright grooves, said shield means having upright edges projected into said grooves.

16. The stadiometer of claim 15 wherein: the edge means includes inwardly directed lips forming said grooves, said upright edges of the shield means extending into said grooves under said lips.

17. An apparatus for measuring the height of an object comprising: an upright rail having at least one upright side section, said rail including upright side walls that converge outwardly toward each other providing the sides of an upright groove in said rail, scale means on said side section having graduations providing information as to the height of the object, slide means movably mounted on said rail for movement along said rail, said slide means having walls located in friction sliding engagement with said side walls of the rail whereby the slide means maintains its adjusted position on the rail and is manually movable to a selected position on the rail, biasing means located in said groove and engageable with said rail to bias the walls of the slide means in friction sliding engagement with said side walls of the rail, means securing the biasing means to said slide means, a generally horizontal arm, means securing said arm to said slide means and extended outwardly away from said rail, shield means secured to the slide means extended over the scale means, means securing the shield means to the slide means, said shield means being movable with the slide means along said rail and relative to the scale means, said shield means having at least a transparent portion located over the scale means whereby the scale means is visible, and means on said transparent portion of the shield means aligned with the arm to provide visual information of the location of the arm relative to the scale means, thereby providing data as to the height of the object when the arm engages the top of the object.

18. The apparatus of claim 17 wherein: the side section of the rail projects rearwardly and laterally relative to the arm.

19. The apparatus of claim 17 wherein: the scale means includes English and metric graduations located in vertical side-by-side relation with equivalent graduations laterally aligned with each other.

20. The apparatus of claim 17 wherein: the means securing said arm to said slide means includes holder means supporting the arm, and means connecting the slide means to the arm and retaining a portion of the arm on the holder means.

21. The apparatus of claim 20 wherein: the holder means includes a transverse groove, and said arm having an end retained in said transverse groove by said means connecting the slide means to the arm.

22. The apparatus of claim 20 wherein: the shield means has a portion located between the holder means and slide means, said means connecting the slide means to the arm clamping the shield means between the holder means and slide means.

23. The apparatus of claim 17 wherein: the biasing means comprises a leaf spring connected to the slide means, said leaf spring having ends located in sliding engagement with the rail.

24. The apparatus of claim 17 wherein: the slide means has a base projected outwardly from the rail, said shield means having a portion mounted on the base whereby the shield means is retained in spaced relation relative to the rail and scale means.

25. The apparatus of claim 17 wherein: low friction means located between said side walls of the rail and the walls of the slide means to facilitate movement of the slide means relative to the rail.

26. The apparatus of claim 17 wherein: the rail has upright edge means having an upright groove on said upright side section, said shield means having an upright edge projected into said groove.

27. The apparatus of claim 26 wherein: the edge means includes an inwardly directed lip forming said groove, said upright edge of the shield means extending into said groove under said lip.

* * * * *